(12) United States Patent
Thirunahari et al.

(10) Patent No.: US 10,464,933 B2
(45) Date of Patent: Nov. 5, 2019

(54) SOLID STATE FORMS OF DASATINIB AND PROCESSES FOR THEIR PREPARATION

(71) Applicant: DR. REDDY'S LABORATORIES LIMITED, Hyderabad (IN)

(72) Inventors: Satyanarayana Thirunahari, Hyderabad (IN); Anish Anil Gupta, Hyderabad (IN); Srividya Ramakrishnan, Hyderabad (IN); Sonawane Swapnil, Pune (IN); Rakeshwar Bandichhor, Sultanpur (IN); Srinivasula Reddy Lakkireddy, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 16/073,963

(22) PCT Filed: Feb. 3, 2017

(86) PCT No.: PCT/IB2017/050593
§ 371 (c)(1),
(2) Date: Jul. 30, 2018

(87) PCT Pub. No.: WO2017/134615
PCT Pub. Date: Aug. 10, 2017

(65) Prior Publication Data
US 2019/0040054 A1 Feb. 7, 2019

(30) Foreign Application Priority Data

Feb. 3, 2016 (IN) .............................. 201641003863
Nov. 4, 2016 (IN) .............................. 201641037736

(51) Int. Cl.
*C07D 417/12* (2006.01)
*C07D 417/14* (2006.01)

(52) U.S. Cl.
CPC ......... *C07D 417/14* (2013.01); *C07D 417/12* (2013.01)

(58) Field of Classification Search
CPC .................................................... C07D 417/12
USPC ......................................................... 544/295
See application file for complete search history.

(56) References Cited

U.S. PATENT DOCUMENTS 7,973,045 B2    7/2011  Simo et al.
2014/0343073 A1 11/2014 Dwivedi et al.

FOREIGN PATENT DOCUMENTS

CN        102040596 A         5/2011
WO        2005077945 A2       8/2005
WO   WO 2009/053854 A2 *      4/2009
WO        2012014149 A1       2/2012

OTHER PUBLICATIONS

Morissette et al., "High-throughput crystallization: polymorphs, salts, co-crystals and solvates of pharmaceutical solids," Advanced Drag Delivery Reviews, 2004, 56:275-300.*
Vippagunta et al., "Crystalline Solids", Advanced Drug Delivery Reviews, 48:3-26, 2001.*
International Search Report dated Apr. 24, 2017, for corresponding International Patent Application No. PCT/IB2017/050593.
Written Opinion dated Apr. 24, 2017, for corresponding International Patent Application No. PCT/IB2017/050593.
International Preliminary Report on Patentability dated Aug. 7, 2018, for corresponding International Patent Application No. PCT/IB2017/050593.

* cited by examiner

*Primary Examiner* — Deepak R Rao
(74) *Attorney, Agent, or Firm* — Pergament & Cepeda LLP; Milagros A. Cepeda; Edward D. Pergament

(57) ABSTRACT

The present invention provides crystalline form of (R)-propylene glycol solvate of dasatinib and crystalline form of (S)-propylene glycol solvate of dasatinib.

4 Claims, 7 Drawing Sheets

$^1$H NMR spectrum of Dasatinib S-propylene glycol solvate in DMSO-d6.

$^{13}$C NMR spectrum of Dasatinib S-propylene glycol solvate in DMSO-$d_6$

SOLID STATE FORMS OF DASATINIB AND PROCESSES FOR THEIR PREPARATION

This application is a National Stage Application under 35 U.S.C. § 371 of PCT International Application No. PCT/IB2017/050593, filed Feb. 3, 2017, which takes priority from Indian Provisional Application Numbers IN 201641003863, filed Feb. 3, 2016; and IN 201641037736, filed Nov. 7, 2016, all of which are herein incorporated in their entireties.

INTRODUCTION

The present invention provides propylene glycol solvates of dasatinib and processes for their preparation.

BACKGROUND OF THE INVENTION

The drug compound having the adopted name "Dasatinib" has a chemical name N-(2-chloro-6-methylphenyl)-2-[[6-[4-(2-hydroxyethyl)-1-piperazinyl]-2-methyl-4-pyridiminyl]amino]-5-thiazolecarboxamide, and is structurally represented by Formula I.

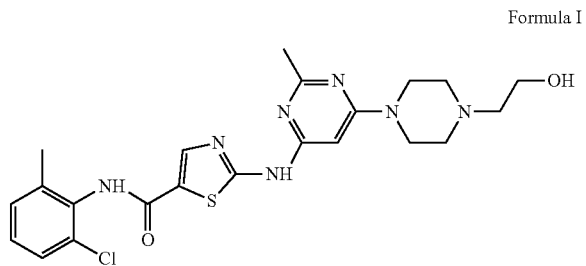 [SMILES: Cc1nc(Nc2ncc(C(=O)Nc3c(C)cccc3Cl)s2)cc(N2CCN(CCO)CC2)n1]

Formula I

Dasatinib is sold under the trade name Sprycel®. Dasatinib is an oral dual BCR/ABL and Src family tyrosine kinases inhibitor approved for use in patients with chronic myelogenous leukemia (CML) after imatinib treatment and Philadelphia chromosome-positive acute lymphoblasticjeukemia (Ph+ ALL).

The PCT application WO2005077945 discloses several crystalline forms of Dasatinib which are designated as monohydrate, butanol solvate, ethanol solvate, crystalline neat form (N-6) and crystalline neat form (T1H1-7).

U.S. Pat. No. 7,973,045 discloses anhydrous form and various other solvates of Dasatinib. US '045 also disclose process for the preparation of amorphous dasatinib by evaporating the solvent from the suspension. The solvents used in the process were selected from dimethylformamide, 1,2-dichlorobenzene, propylene glycol, ethylene glycol and glycerol. Example 60 of US '045 discloses preparation of amorphous Dasatinib by slurring in propylene glycol and heating.

US20140343073A1 discloses process for the preparation of amorphous form of dasatinib by milling.

Dasatinib prepared by the methods known in the art contain related substances or impurities. These impurities can be unreacted starting materials, by-products of the reaction, products of side reactions, or degradation products. One such impurity encountered in the Dasatinib Propylene Glycol solvate is the N-oxide impurity. The peroxide content in the Propylene Glycol solvent and environmental oxygen are the two sources for N-Oxide impurity formation during crystallization of Dasatinib.

The autoxidation and the exposure to atmospheric oxygen of certain organic solvents during storage result in the peroxide formation in such solvents. The uses of peroxide containing solvents for substances which are easily oxidized require the prior removal of accumulated peroxides. Also, peroxides concentration in the solvents can be minimized by using various techniques such as adsorption using activated carbon, alumina etc. or by chemical reduction such as use of antioxidants (Journal of Pharmaceutical Sciences, Volume 101, Issue 1, January 2012, Pages 127-139; Ind. Eng. Chem. Anal. Ed., 1946, 18 (1), pp 52-54).

Generally, impurities are identified spectroscopically and/or with another physical method, and then are associated with peak position, such as that in a chromatogram, or spot on a TLC plate. Thereafter, the impurity can be identified, e.g., by its relative position in the chromatogram, where the position in a chromatogram is measure in minutes between injection of the sample on the column and elution of the particular component through the detector. The relative position in the chromatogram is known as the "retention time."

Retention time can vary about a mean value based upon the condition of the instrumentation as well as many other factors. To mitigate the effects such variations have upon accurate identification of an impurity, those skilled in the art use the "relative retention time" (RRT) to identify impurities. The RRT of an impurity is its retention time divided by the retention time of a reference marker.

The management of process related impurities is enhanced by understanding their chemical structures and synthetic pathways, and by identifying the parameters that influence the amount of impurities in the final product.

It is desirable that there is a method for identifying, quantifying and separating the impurities formed as a result of the synthesis of Dasatinib.

An objective of the present invention is to provide a method for preparation of Dasatinib with high purity.

For a compound to be suitable for use as a therapeutic agent, the physical properties of the compound should be such that they do not negatively impact the effectiveness and cost of a formulated active ingredient.

The inventors of the present invention have surprisingly found a novel crystalline form of dasatinib and processes for their preparation.

SUMMARY OF THE INVENTION

In an aspect, the present invention provides crystalline form of (R)-propylene glycol solvate of Dasatinib.

In an aspect, the present invention provides (R)-propylene glycol solvate of Dasatinib characterized by PXRD pattern as shown in FIG. 1.

In an aspect, the present invention provides (R)-propylene glycol solvate of Dasatinib characterized by PXRD pattern having peaks at about 15.02, 17.93, 21.19 and 22.91±0.20 degrees 2-theta and also having peaks at about 6.03, 11.98, 18.21, 21.42, 24.10, 24.55, 26.17 and 28.05±0.20 degrees 2-theta.

In an aspect, the present invention provides crystalline form of (S)-propylene glycol solvate of Dasatinib.

In an aspect, the present invention provides (S)-propylene glycol solvate of Dasatinib characterized by PXRD pattern as shown in FIG. 2.

In an aspect, the present invention provides (S)-propylene glycol solvate of Dasatinib characterized by PXRD pattern having peaks at about 15.02, 17.93, 21.19 and 22.91±0.20 degrees 2-theta and also having peaks at about 6.03, 11.98, 18.21, 21.42, 24.10, 24.55, 26.17 and 28.05±0.20 degrees 2-theta.

In an aspect, the present invention provides processes for the preparation of (R)-propylene glycol solvate of Dasatinib and (S)-propylene glycol solvate of Dasatinib.

In an aspect, the present invention provides a process for the preparation of Dasatinib, substantially free from the N-oxide impurity of dasatinib.

In another aspect, the present invention provides a pharmaceutical composition comprising highly pure Dasatinib substantially free of Dasatinib N-oxide impurity, and one or more pharmaceutically acceptable excipients.

DETAILED DESCRIPTION

In an aspect, the present invention provides crystalline form of (R)-propylene glycol solvate of Dasatinib.

Figure 1:
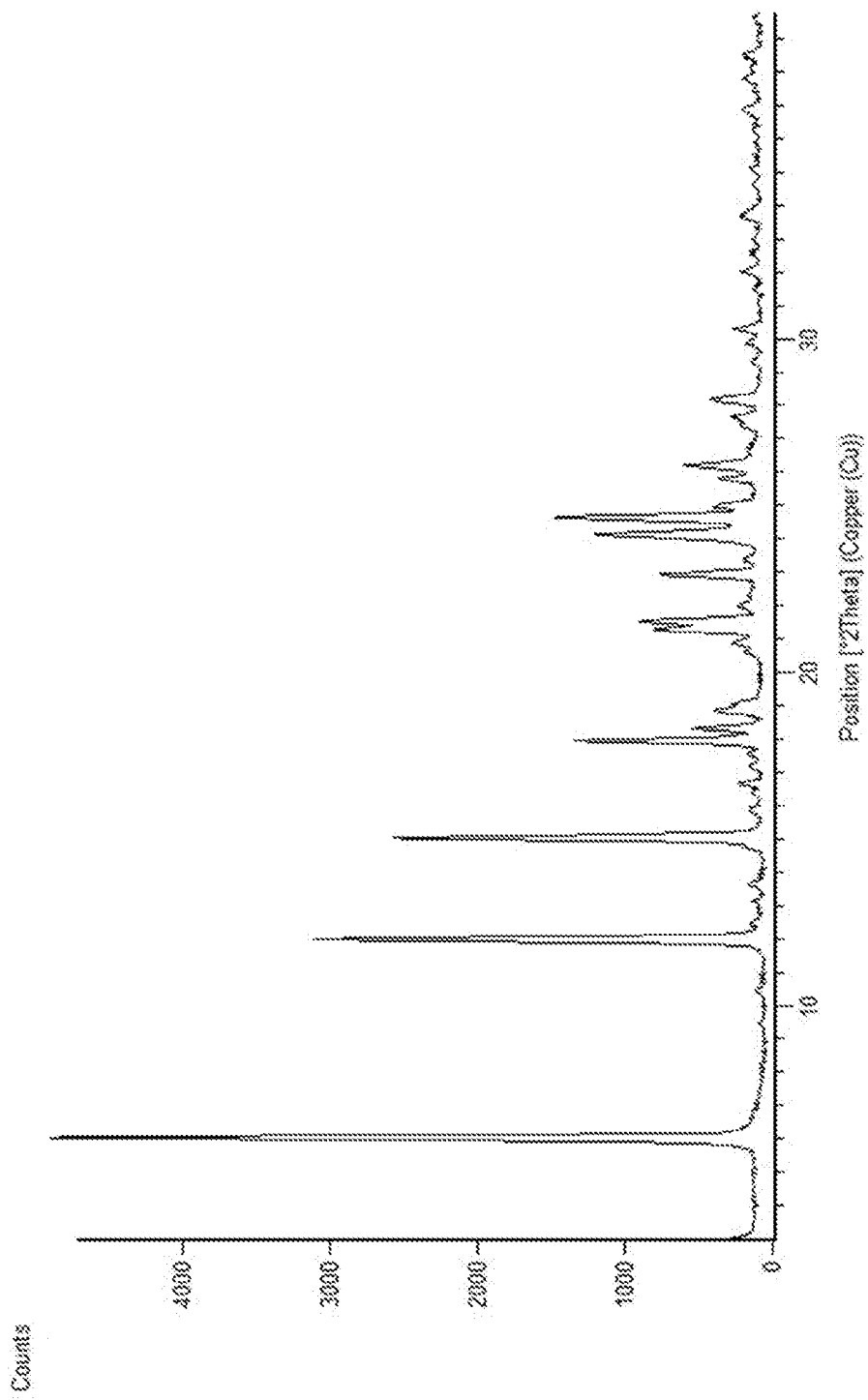
FIG. 1 illustrates the PXRD pattern of (R)-propylene glycol solvate of Dasatinib.

In an aspect, the present invention provides (R)-propylene glycol solvate of Dasatinib characterized by PXRD pattern as shown in FIG. 1.

In an aspect, the present invention provides (R)-propylene glycol solvate of Dasatinib characterized by PXRD pattern having peaks at about 15.02, 17.93, 21.19 and 22.91±0.20 degrees 2-theta and also having peaks at about 6.03, 11.98, 18.21, 21.42, 24.10, 24.55, 26.17 and 28.05±0.20 degrees 2-theta.

In an aspect, the present invention provides process for the preparation of (R)-propylene glycol solvate of Dasatinib, comprising the steps of:
a) mixing dasatinib and (R)-propylene glycol;
b) heating the reaction mixture at 70-150° C.;
c) cooling the reaction mixture to a temperature between 30 to 60° C.;
d) isolating the crystalline form of dasatinib.

In step a) either dasatinib is added to (R)-propylene glycol or (R)-propylene glycol is added to dasatinib at temperature of about 0° C. to about 50° C., preferably at about 10° C. to about 40° C., more preferably at about 25° C. to about 35° C. The ratio of dasatinib to propylene glycol may vary from about 1:5 to 1:25 by volume. Preferably the ratio is about 1:10 to 1:25 by volume.

Step b) comprises heating the reaction mixture at 70-150° C. In an embodiment, the reaction mixture of step a) is heated at a temperature of about 70° C. to about 130° C., more preferably at about 70° C. to about 100° C. and stirring was performed for a time period of about 30 minutes to about 24 hours.

Step c) involves cooling the reaction mixture in between 30° C. to 70° C. In a preferred embodiment, the reaction mixture is cooled to 40-60° C. The reaction mixture is maintained for a sufficient time to ensure the formation of R-propylene glycol solvate of dasatinib. The crystalline (R)-propylene glycol solvate of dasatinib is isolated in a manner known per se, which include, but not limited to filtration by gravity or by suction/vacuum, distillation, centrifugation, or slow evaporation or the like. In an embodiment, crystalline (R)-propylene glycol solvate of dasatinib may be isolated by filtration under vacuum and suction drying at a temperature of about 30° C. to about 60° C.

In an aspect, the present invention provides crystalline form of (S)-propylene glycol solvate of Dasatinib.

Figure 2:
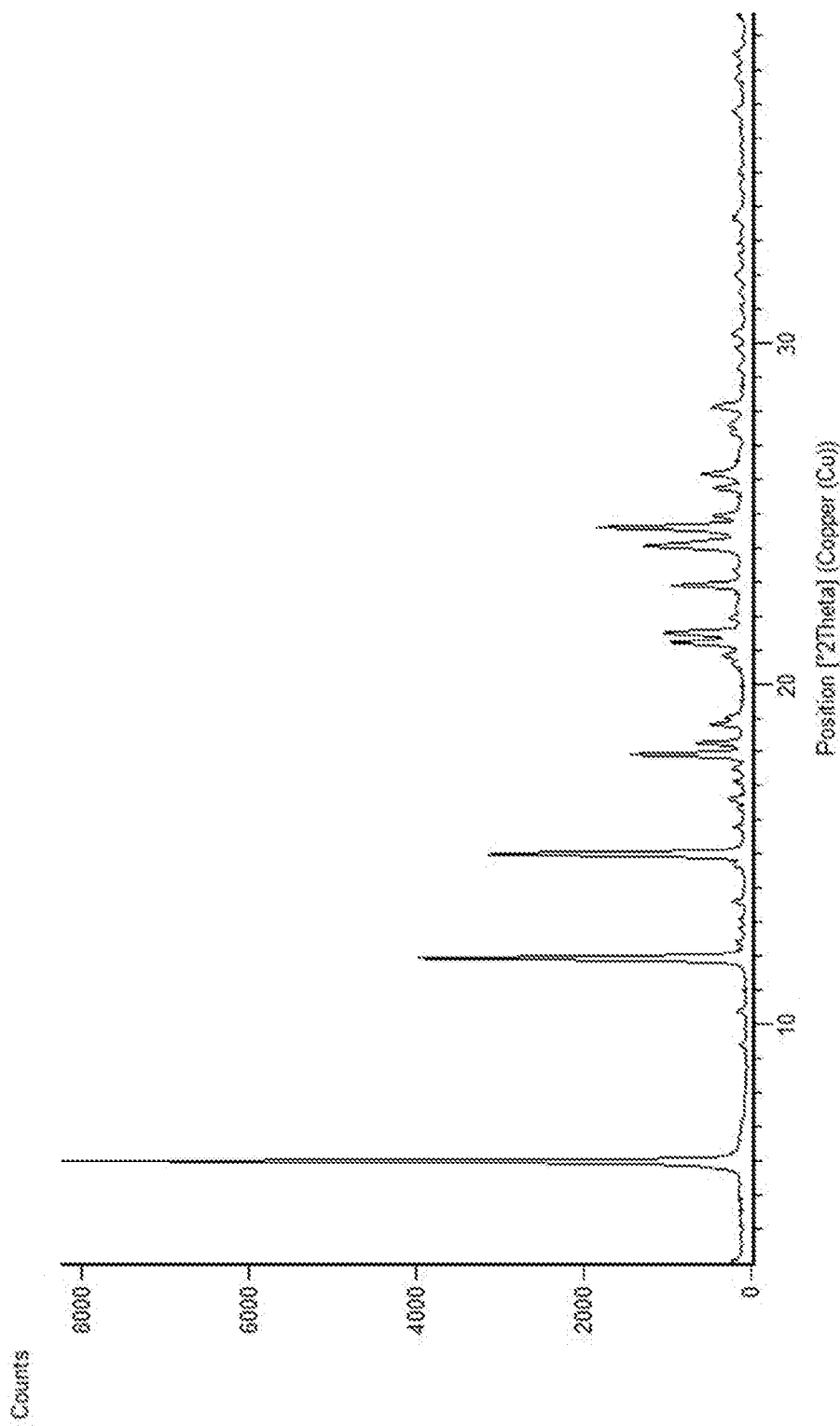
FIG. 2 illustrates the PXRD pattern of (S)-propylene glycol solvate of Dasatinib.
Figure 3:
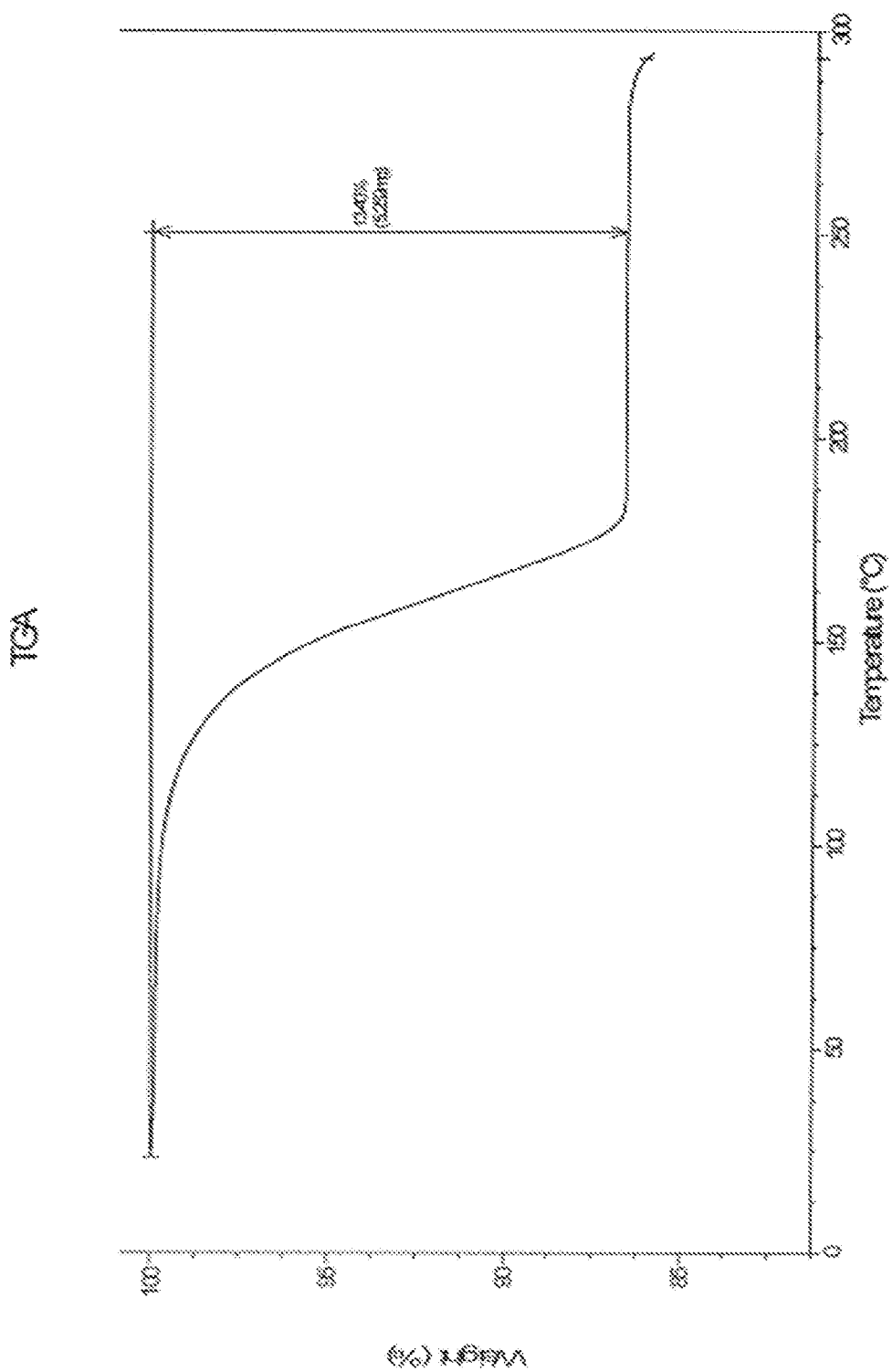
FIG. 3 illustrates TG analysis of Dasatinib (S)-propylene glycol solvate.
Figure 4:
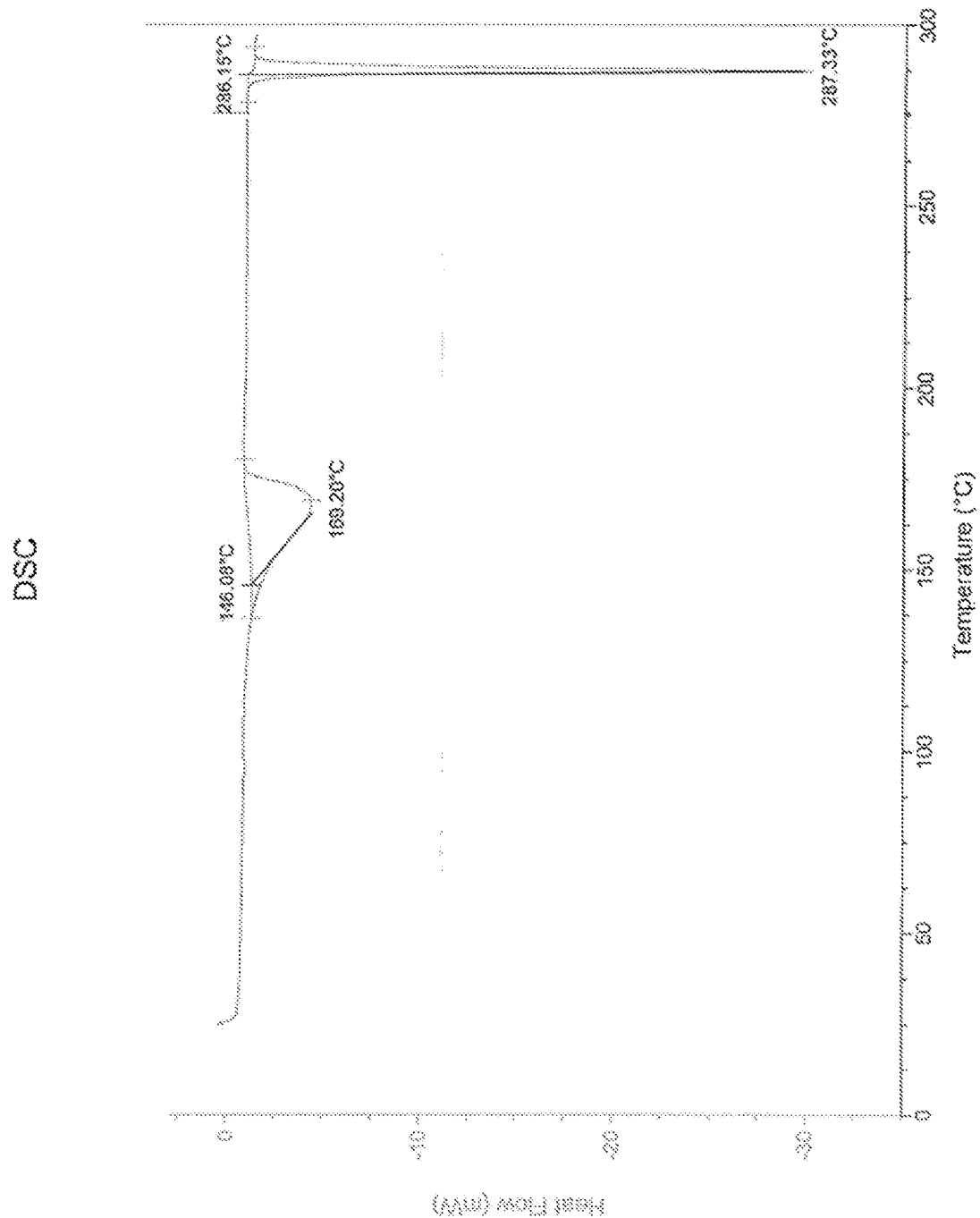
FIG. 4 illustrates DSC thermogram of Dasatinib (S)-propylene glycol solvate.
Figure 5:
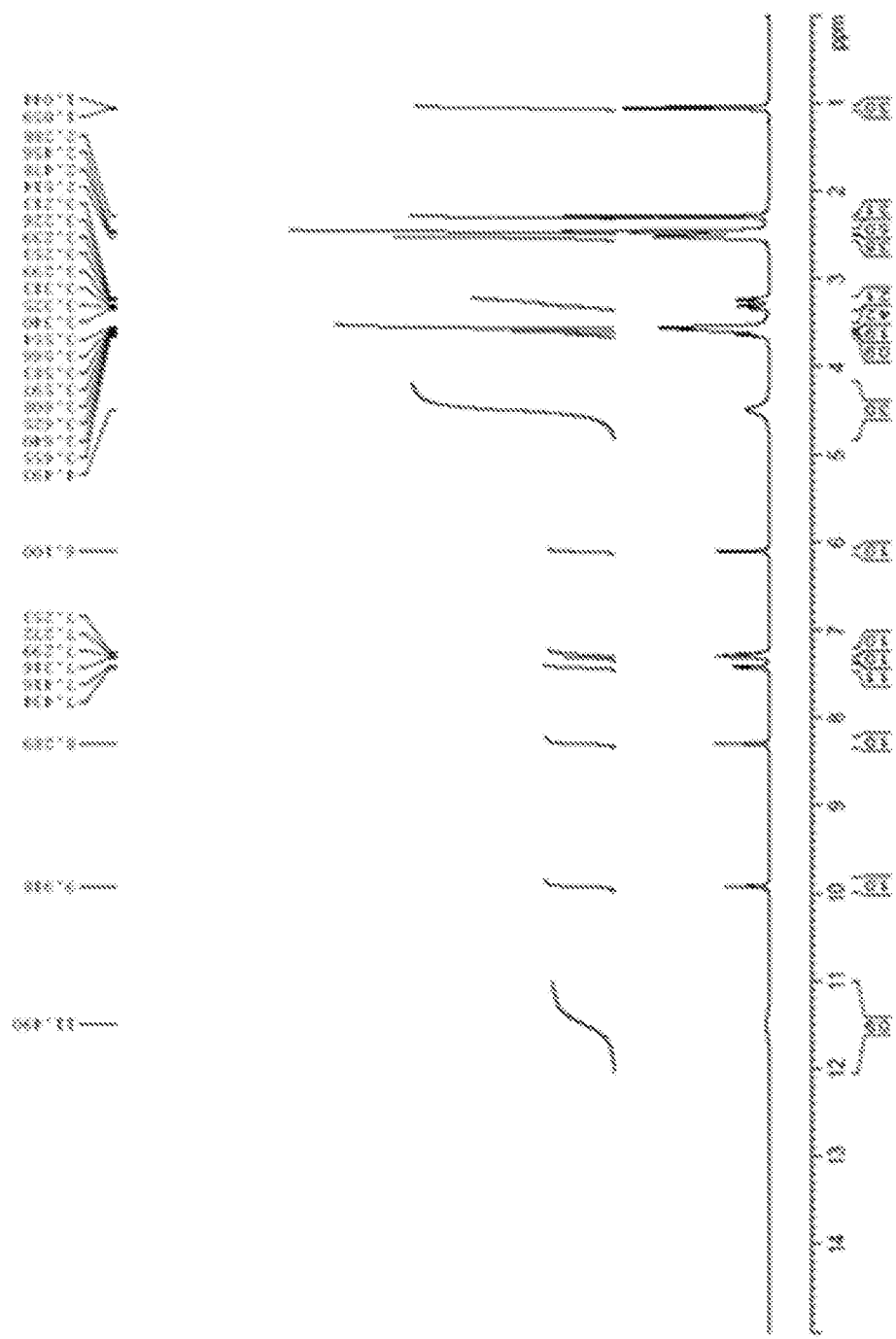
FIG. 5 illustrates $^1$H NMR spectrum of Dasatinib (S)-propylene glycol solvate in DMSO-d6.
Figure 6:
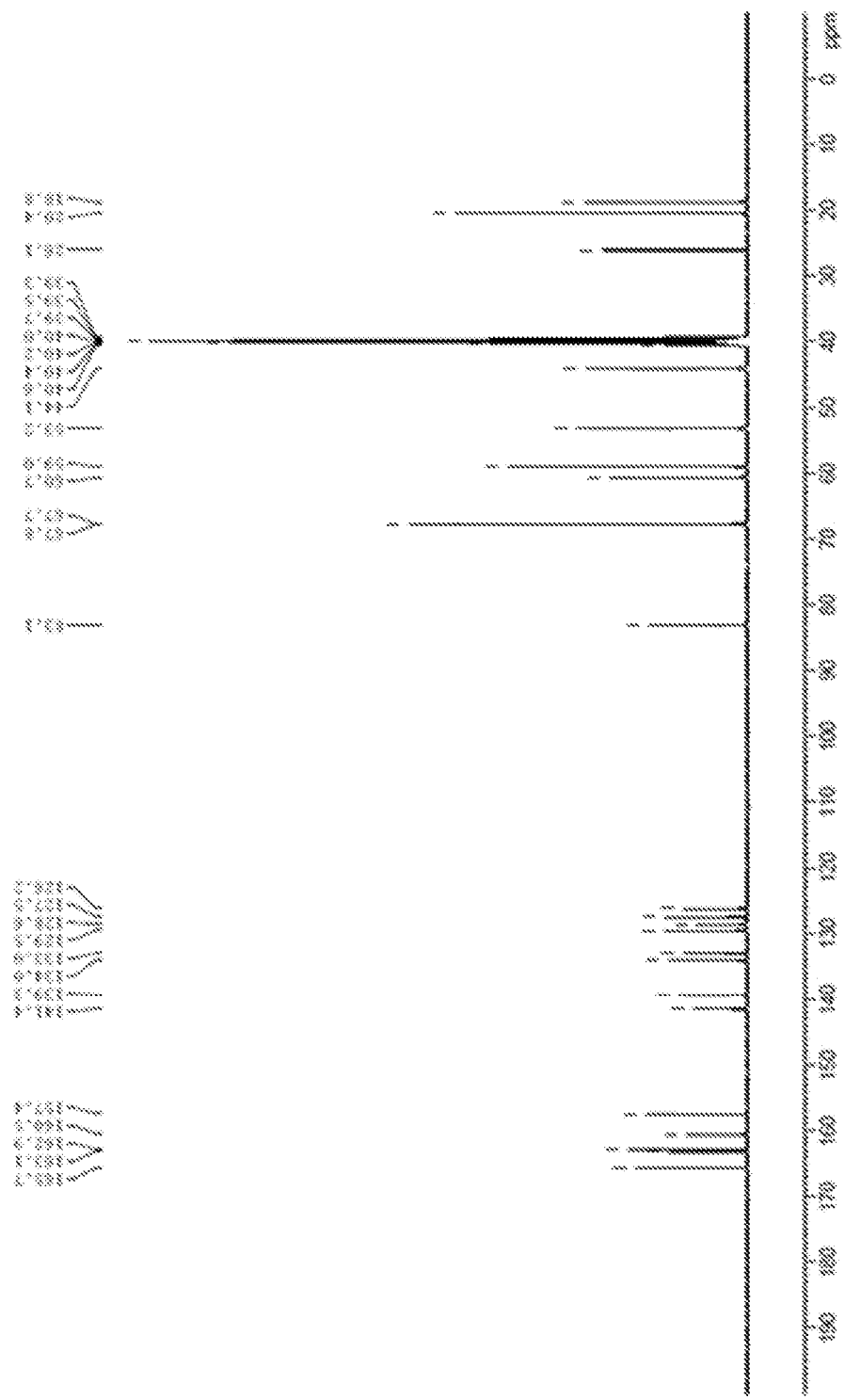
FIG. 6 illustrates $^{13}$C NMR spectrum of Dasatinib (S)-propylene glycol solvate in DMSO-d6.
Figure 7:
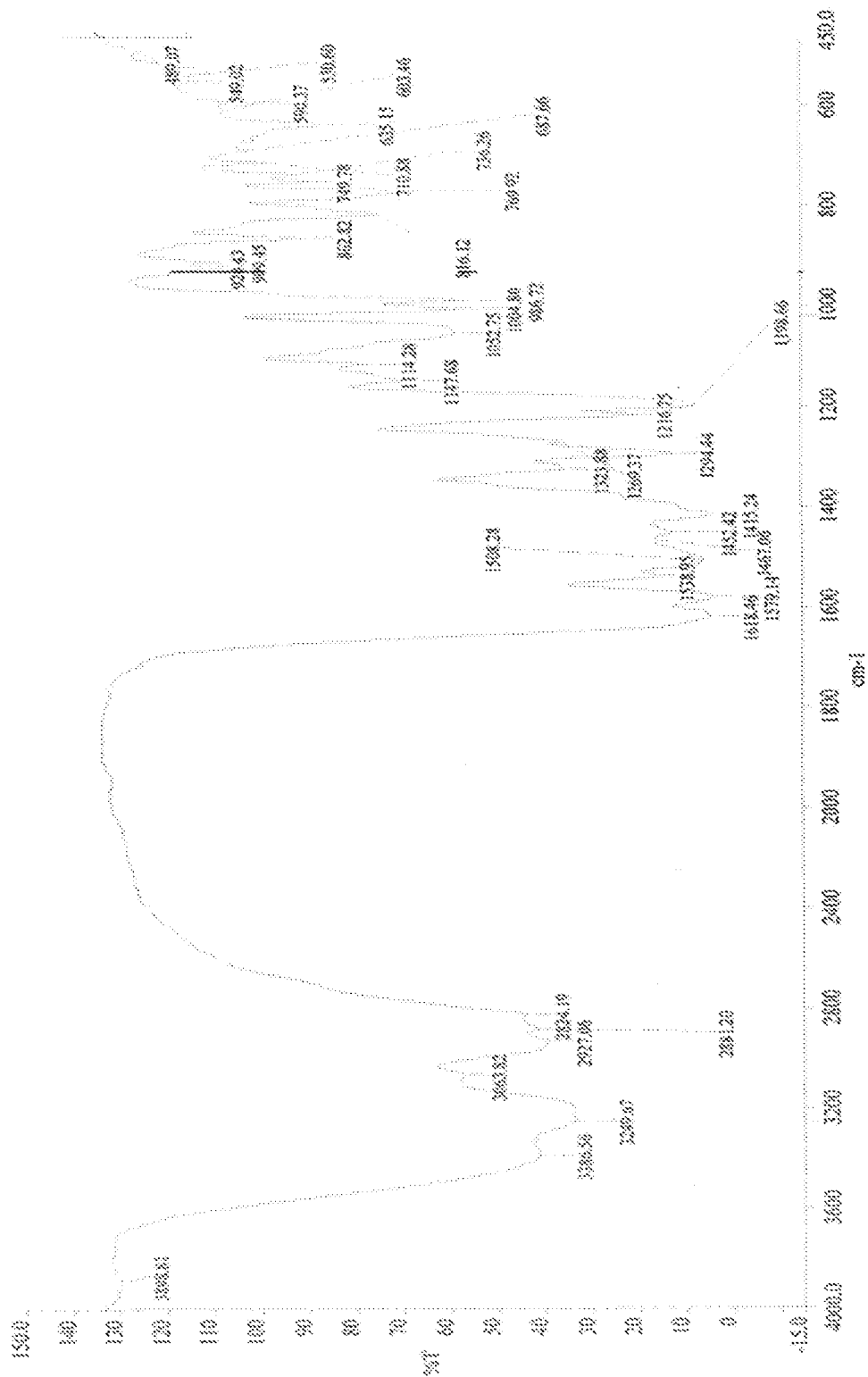
FIG. 7 illustrates FT-IR spectrum of Dasatinib (S)-propylene glycol solvate.

In an aspect, the present invention provides (S)-propylene glycol solvate of Dasatinib characterized by PXRD pattern as shown in FIG. 2.

In an aspect, the present invention provides (S)-propylene glycol solvate of Dasatinib characterized by PXRD pattern having peaks at about 15.02, 17.93, 21.19 and 22.91±0.20 degrees 2-theta and also having peaks at about 6.03, 11.98, 18.21, 21.42, 24.10, 24.55, 26.17 and 28.05±0.20 degrees 2-theta.

In an aspect, the present invention provides process for the preparation of (S)-propylene glycol solvate of Dasatinib, comprising the steps of:
a) mixing dasatinib and (S)-propylene glycol;
b) heating the reaction mixture at 70-150° C.;
c) cooling the reaction mixture to a temperature between 30 to 60° C.;
d) isolating the crystalline form of dasatinib.

In step a) either dasatinib is added to (S)-propylene glycol or (S)-propylene glycol is added to dasatinib at temperature of about 0° C. to about 50° C., preferably at about 10° C. to about 40° C., more preferably at about 25° C. to about 35° C. The ratio of dasatinib to propylene glycol may vary from about 1:5 to 1:25 by volume. Preferably the ratio is about 1:10 to 1:25 by volume.

Step b) comprises heating the reaction mixture at 70-150° C. In an embodiment, the reaction mixture of step a) is heated at a temperature of about 70° C. to about 130° C., more preferably at about 70° C. to about 100° C. and stirring was performed for a time period of about 30 minutes to about 24 hours.

Step c) involves cooling the reaction mixture in between 30° C. to 70° C. In a preferred embodiment, the reaction mixture is cooled to 40-60° C. The reaction mixture is maintained for a sufficient time to ensure the formation of S-propylene glycol solvate of dasatinib. The crystalline (S)-propylene glycol solvate of dasatinib is isolated in a manner known per se, which include, but not limited to filtration by gravity or by suction/vacuum, distillation, centrifugation, or slow evaporation or the like. In an embodiment, crystalline (S)-propylene glycol solvate of dasatinib may be isolated by filtration under vacuum and suction drying at a temperature of about 30° C. to about 60° C.

The N-oxide impurity of dasatinib disclosed herein is represented by the formula II.

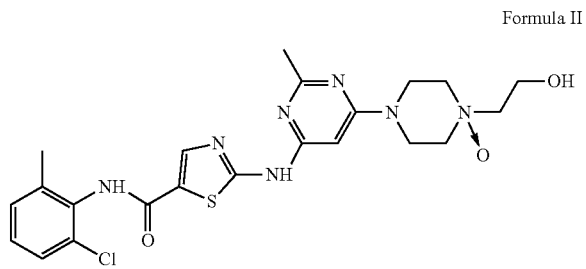 [SMILES: Cc1nc(Nc2ncc(C(=O)Nc3c(C)cccc3Cl)s2)cc(N2CC[N+]([O-])(CCO)CC2)n1]

Formula II

In an embodiment, the present invention provides process for the preparation of Dasatinib substantially free of N-oxide impurity, comprising the steps of:
a) treating propylene glycol solvent with antioxidant;
b) contacting the treated propylene glycol solvent with Dasatinib;
c) maintaining and filtering the propylene glycol solvate of Dasatinib;
d) optionally, drying the propylene glycol solvate of Dasatinib.

Prior to step a) the propylene glycol solvent is optionally treated with an adsorbing agent such as activated carbon, alumina or the like in an inert atmosphere.

The antioxidant used in step a) is selected from propyl gallate, sodium sulfite, butylated hydroxyanisole (BHA), or butylated hydroxytoluene (BHT) and the like or mixtures thereof.

In one embodiment, the reaction in step (a) is carried out in an inert atmosphere at a temperature of about 60° C. to about the reflux temperature of propylene glycol, specifically at about 60° C. to about 100° C., and more specifically at about 60° C. to about 80° C.

In another embodiment, the propylene glycol solvent used in step a) can be selected from racemic propylene glycol, R-propylene glycol or S-propylene glycol. In a preferred embodiment, S-propylene glycol solvent is used.

In another embodiment, the reaction in step (b) is heated to a temperature of about 40° C. to the reflux temperature of the solvent and more specifically to about 60-100° C. about 30 minutes to about 10 hours.

In step c), the solvent is removed by filtration and is carried out at a temperature of about 40-70° C. under inert atmosphere.

Drying in step d) may be suitably carried out using any equipment such as a gravity oven, tray dryer, vacuum oven, Rotavapor®, air tray dryer, fluidized bed dryer, spin flash dryer, flash dryer, and the like. In an embodiment, the drying may be carried out at atmospheric pressure or under reduced pressure or under inert atmosphere. In an embodiment, the drying may be carried out at a temperature of about 70° C., at a temperature of about 60° C., at a temperature of about 50° C. or at a temperature of about 40° C. The drying may be carried out for any time periods required for obtaining a desired quality, such as from about 15 minutes to several hours, or longer.

Dasatinib substantially free of N-oxide impurity refers to Dasatinib and/or one or more pharmaceutically acceptable excipients thereof comprising the Dasatinib N-oxide impurity in an amount of less than about 0.25 area % as measured by HPLC. Specifically, the Dasatinib, as disclosed herein, contains less than about 0.15 area %, more specifically less than about 0.05 area %, still more specifically less than about 0.02 area % of the dasatinib N-oxide impurity, and most specifically is essentially free of the dasatinib N-oxide impurity.

In another embodiment, Dasatinib or Dasatinib with one or more pharmaceutically acceptable excipients has a purity of greater than about 99%, specifically greater than about 99.5%, more specifically greater than about 99.9%, and most specifically greater than about 99.95% as measured by HPLC. For example, the purity of Dasatinib or Dasatinib with one or more pharmaceutically acceptable excipients is about 99% to about 99.95%, or about 99.5% to about 99.99%.

Certain specific aspects and embodiments of the present invention will be explained in more detail with reference to the following examples, which are provided only for purposes of illustration and should not be construed as limiting the scope of the present application in any manner.

HPLC Conditions:

| Column | SYMMETRY C18, 250 mm × 4.6 mm, 5.0 µm |
| --- | --- |
| Flow rate | 1.0 ml/min |
| Column oven temperature | 30° C. |
| Wave length | 320 nm |
| Injection Volume | 10 ul |
| Run time | 60 min |
| Diluent | Acetonitrile:water (1:1) |

| | Time (min) | % Mobile Phase A | % Mobile Phase B |
| --- | --- | --- | --- |
| Gradient program | 0.0 | 80 | 20 |
| | 20.0 | 60 | 40 |
| | 42.0 | 20 | 80 |
| | 50.0 | 20 | 80 |
| | 55.0 | 80 | 20 |
| | 60.0 | 80 | 20 |

Sample concentration: 0.5 mg/mL
Mobile phase-A: Buffer: Dissolved 1.3 g of Ammonium Formate in 1000 mL of water and adjusted the pH to 3.00 with formic acid.
Mobile phase-B: Acetonitrile.
The following examples further illustrate the invention but should not be construed as in any way limiting its scope.
General Description of the PXRD Equipment:
X-ray diffraction was measured using PANalytical X-ray diffractometer, Model: X'Pert PRO. System description: CuK-Alpha 1 wavelength=1.54060, voltage 45 kV, current 40 mA, divergence slit=0.5°; Sample stage=Reflection-Transmission Spinner. Scan type: Continuous; Detector-X'Celerator; Measurement parameters: Start Position [° 2Th.]: 3; End Position [° 2Th.]: 40; Step Size [° 2Th.]: 0.0170; Scan Step Time [s]: 22.86.

EXAMPLES

Example 1: Preparation of (R)-Propylene Glycol Solvate of Dasatinib 0.2 g of dasatinib and 3 mL of (R)-propylene glycol were charged into a reactor at 25 to 30° C. The contents were stirred and heated to 120° C. and maintained for 1-2 hours. The contents were then cooled to 20-30° C. The obtained material was filtered and dried in vacuum tray dryer at 60° C. to afford (R)-propylene glycol solvate of dasatinib characterized by PXRD pattern as shown in FIG. 1.

Example 2: Preparation of (S)-Propylene Glycol Solvate of Dasatinib 0.2 g of dasatinib and 3 mL of S-propylene glycol were charged into a reactor at 25 to 30° C. The contents were stirred and heated to 120° C. and maintained for 1-2 hours. The contents were then cooled to 20-30° C. The obtained material was filtered and dried in vacuum tray dryer at 60° C. to afford (S)-propylene glycol solvate of dasatinib characterized by PXRD pattern as shown in FIG. 2.

Example 3: Preparation of Dasatinib N-Oxide 50.0 g of N-(2-chloro-6-methylphenyl)-2-((6-(4-(2-hydroxyethyl)piperazin-1-yl)-2-methylpyrimidin-4-yl)amino)thiazole-5-carboxamide and 365 mL of N-Methyl-2-pyrrolidone were taken in flask and 131 g of 30% hydrogen peroxide was added to it. The contents were maintained for overnight and filtered. The contents were washed with De-mineralized water and suck dried. The obtained material was dried under reduced pressure at 40° C. 10-12 hours to obtain the titled compound.

HPLC: 99.9% purity; Retention time: 17.4

LC/MS (M-H) calculated for N-oxide impurity: 502.15; Found: 502.0.

$^1$H NMR (400 MHz, DMSO-d6) δ 7.18-7.3 (m, 1H), 7.18-7.3 (m, 1H), 7.36-7.41 (m, 1H), 2.21 (s, 3H), 9.80 (s, NH—CO), 8.20 (s, 1H), 6.13 (s, 1H), 2.42 (s, 3H), 3.65-4.12 (m, 4H), 3.88-4.16 (m, 4H), 3.18-3.40 (m, 2H), 3.91 (t, 2H).

Example 4: Preparation of Dasatinib S-Propylene Glycol Solvate 3.0 g of Dasatinib and 45 mL of S-propylene glycol solvent were charged into a reactor at 25° C. and heated to 100° C. The contents were stirred at the same temperature and cooled to 60° C. and filtered, followed by drying in vacuum tray dryer at 60° C. to afford the title compound.

HPLC Purity: 99.31%; N-oxide impurity: 0.61% (RRT: 1.12).

Example 5: Preparation of Dasatinib S-Propylene Glycol Solvate 60 mL of S-propylene glycol was taken in a reactor and 4 g of activated carbon SC-40 grade was added to it and stirred for 60-70 minutes at 60° C. The resulting solution was filtered on hyflow-bed and the obtained solvent was taken in a reactor and to it was added 4 g of dasatinib. The contents were stirred and heated to 100° C. for 90-120 minutes. The contents were cooled to 60° C. and filtered, followed by drying in vacuum tray dryer at 60° C. to afford the title compound.

HPLC Purity: 99.89%; N-oxide impurity: 0.1% (RRT: 1.12).

Example 6: Preparation of Dasatinib S-Propylene Glycol Solvate 420 mL of S-propylene glycol was taken in a reactor and 0.42 g of BHT was added to it and heated to 40-45° C. To this solution was added 35 g of dasatinib and heated to 80-85° C. The contents were maintained for 3-4 hours and cooled to 60-65° C. The reaction was filtered and dried in vacuum tray dryer at 60° C. to afford the title compound.

HPLC Purity: 99.91%; N-oxide impurity: 0.03% (RRT: 1.12).

Example 7: Preparation of Dasatinib (S)-Propylene Glycol Solvate (S)-Propylene glycol solvate (12 Liter) was treated with activated carbon SC-40 at 70-80° C. under nitrogen atmosphere and transferred to a clean reactor and cooled to 20-30° C. 12.0 g of Butylated hydroxy toluene (BHT) was added to this reactor and heated to 75-80° C. Dasatinib (1000 g, 250×4 lots) was added lot wise to the above reactor at 75-80° C. and maintained till the completion of the reaction. The reaction mass was filtered through Agitated Nutsche Filter Dryer at 60±5° C. and dried under nitrogen atmosphere to obtain the title compound.

HPLC purity: 99.94%; N-oxide impurity: 0.02%

The invention claimed is:

1. A crystalline form of Dasatinib (S)-propylene glycol solvate.

2. The crystalline form of Dasatinib (S)-propylene glycol solvate characterized by PXRD pattern as shown in FIG. 2.

3. The crystalline form according to claim 2, characterized by an X-ray powder diffraction pattern having peaks at about 15.02, 17.93, 21.19 and 22.91±0.20 degrees 2-theta and also having peaks at about 6.03, 11.98, 18.21, 21.42, 24.10, 24.55, 26.17 and 28.05±0.20 degrees 2-theta.

4. A process for preparing Dasatinib (S)-propylene glycol solvate, comprising the steps of:
   a) optionally, treating the (S)-propylene glycol solvent with antioxidant;
   b) mixing dasatinib and (S)-propylene glycol solvent;
   c) maintaining and isolating the propylene glycol solvate of Dasatinib; and
   d) optionally, drying the propylene glycol solvate of Dasatinib.

* * * * *